US006335003B1

(12) United States Patent
Kim et al.

(10) Patent No.: US 6,335,003 B1
(45) Date of Patent: Jan. 1, 2002

(54) USE OF CATIONIC POLYURETHANES AND POLYUREAS AS INGREDIENTS OF COSMETIC PREPARATIONS

(75) Inventors: Son Nguyen Kim, Hemsbach; Axel Sanner, Frankenthal; Karin Sperling-Vietmeier, Neustadt; Peter Hoessel, Schifferstadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 08/424,527

(22) PCT Filed: Nov. 25, 1993

(86) PCT No.: PCT/EP93/03306

§ 371 Date: May 30, 1995

§ 102(e) Date: May 30, 1995

(87) PCT Pub. No.: WO94/13724

PCT Pub. Date: Jun. 23, 1994

(30) Foreign Application Priority Data

Dec. 7, 1992 (DE) .......................................... 42 41 118

(51) Int. Cl.[7] .............................. A61K 7/11; A61K 7/06; C08G 18/32
(52) U.S. Cl. ................ 424/70.17; 424/70.1; 424/70.11; 528/61; 528/65
(58) Field of Search ............................. 424/70.17, 70.1, 424/70.11; 528/61, 65

(56) References Cited

U.S. PATENT DOCUMENTS 4,013,787 A * 3/1977 Varlerberghe et al. ... 424/70.17
4,166,845 A * 9/1979 Hansen et al. .............. 514/401

FOREIGN PATENT DOCUMENTS

| DE | 1 178 586 | | 12/1962 |
| EP | 0433776 | * | 6/1990 |
| GB | 2114580 | * | 8/1983 |

* cited by examiner

*Primary Examiner*—Thurman K. Page
*Assistant Examiner*—Brian K. Seidleck
(74) *Attorney, Agent, or Firm*—Oblon, Spivak, McClelland, Maier & Neustadt, P.C.

(57) ABSTRACT

Cationic polyurethanes and polyureas formed from
(a) at least one diisocyanate or reaction product thereof with one or more compounds containing two or more active hydrogen atoms per molecule, and
(b) at least one diol, primary or secondary amino alcohol, primary or secondary diamine or primary or secondary triamine each with one or more tertiary, quaternary or protonated tertiary amine nitrogen atoms and having a glass transition temperature of at least 25 ° C. and an amine number of from 50 to 200, based on the non-quaternized or -protonated compounds, or other salts of these polyurethanes and polyureas, are useful as ingredients of cosmetic and pharmaceutical preparations.

4 Claims, No Drawings

USE OF CATIONIC POLYURETHANES AND POLYUREAS AS INGREDIENTS OF COSMETIC PREPARATIONS

This application is a 371 of PCT/EP 93/03306, filed Nov. 25, 1993.

The present invention relates to the use of cationic polyurethanes and polyureas as ingredients of cosmetic and pharmaceutical preparations. Since some of these compounds are new, the invention further relates to these novel polyurethanes and polyureas.

Polyurethanes and polyureas which contain cationic groups through incorporation of quaternizable or protonatable tertiary amine nitrogen atoms are known. For instance, DE-A-20 19 324 (1) describes lightfast polyurethane ionomers with tertiary or quaternary ammonium nitrogen which contain structural units of the formula

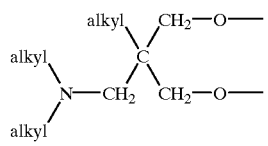

in which the nitrogen atom can be quaternized or protonated. These polyurethane ionomers are recommended for a very wide range of applications, but the cosmetics and pharmaceutical sectors are not mentioned.

DE-C-11 78 586 (2) discloses polyurethanes based on polyhydroxy compounds having a molecular weight of from 400 to 10,000 and polyisocyanates wherein at least one of the components contains at least one basic tertiary amine nitrogen atom. For instance, Example 14 describes the preparation of a polyurethane from an adipic acid-hexanediol polyester, toluylene diisocyanate, 1,4-butanediol and a small amount of N-methyldiethanolamine. The polyurethane of Example 14 can be calculated to have an amine number of 27. These polyurethanes are recommended inter alia for use as hair setting agents.

In cosmetics, hair dressings, for example in the form of lotions or sprays, are used for fixing, controlling and shaping the hair. Hair dressings consist predominantly of a solution of film-forming resins or synthetic polymers. Hitherto hair dressings were chiefly based on the following film formers: shellac, homo- and copolymers of N-vinylpyrrolidone, copolymers of vinyl ethers/maleic monoesters, of (meth)acrylic acid or their esters and amides and crotonic acid with vinyl esters.

The hair dressings are applied to the hair in the form of solutions, preferably as ethanolic solutions, by spraying. The solvent evaporates to leave behind a polymer which fixes the hair strands in the desired shape at the mutual contact points. The polymer should on the one hand be sufficiently hydrophilic that it can be washed out of the hair, on the other it should be hydrophobic in order that the hair treated therewith keeps its shape, and does not become sticky, even under high atmospheric humidity.

However, the prior art polymeric film-formers such as polyvinylpyrrolidone usually have the disadvantage of excessive water absorption at elevated humidity. This property leads inter alia to an undesirable stickiness of the hair and to a loss of the hold and hence to a collapse of the hairstyle. If, on the other hand, the resistance to high humidity is improved, for example in the case of copolymers of N-vinylpyrrolidone and vinyl acetate, this jeopardizes the elasticity of the film, and the brittleness of these films can even lead to an unpleasant dusting and a flaky appearance. Moreover, it is difficult to get the hair completely clean. The abovementioned synthetic hair dressings are nonbiodegradable because of their hydrolysis-resistant carbon-carbon chain. Shellac, by contrast, is biodegradable, but has many disadvantages. For instance, its performance characteristics as a hair dressing are worse compared with the homo- and copolymers of N-vinylpyrrolidone, especially as regards tackiness, water solubility and stiffness. Since shellac is a natural product, its properties are subject to great fluctuations.

It is an object of the present invention to provide ingredients for cosmetic and pharmaceutical preparations which are free of the above-described disadvantages of the prior art.

We have found that this object is achieved by the use of cationic polyurethanes and polyureas formed from
(a) at least one diisocyanate or reaction product thereof with one or more compounds containing two or more active hydrogen atoms per molecule, and
(b) at least one diol, primary or secondary amino alcohol, primary or secondary diamine or primary or secondary triamine each with one or more tertiary, quaternary or protonated tertiary amine nitrogen atoms and having a glass transition temperature of at least 25° C. and an amine number of from 50 to 200, based on the non-quaternized or -protonated compounds, or other salts of these polyurethanes and polyureas, as ingredients of cosmetic and pharmaceutical preparations.

Suitable compounds of group (a) include in particular $C_2$- to $C_8$-alkylene diisocyanates, eg. 1,2-ethylene diisocyanate, 1,4-butylene diisocyanate, hexamethylene diisocyanate or octamethylene diisocyanate, $C_5$- to $C_{10}$-cycloalkylene diisocyanates, eg. 1,3-cyclopentylene diisocyanate, 1,3- or 1,4-cyclohexylene diisocyanate or isophorone diisocyanate, o-, m- or p-phenylene diisocyanate or ($C_1$- to $C_4$-alkyl) phenylene diisocyanates, eg. toluylene diisocyanate. These diisocyanates may have already been reacted with one or more compounds selected from the group consisting of diols, amino alcohols, diamines, polyesterols, polyamidediamines and polyetherols each with a number average molecular weight of up to 2000, although up to 3 mol % of the last-mentioned compounds may be replaced by triols or triamines and the diols and aminoalcohols may contain one or more tertiary, quaternary or protonated tertiary amine nitrogen atoms.

Suitable diols include for example ethylene glycol, propylene glycol, butylene glycol, neopentylglycol, polyetherols such as polyethylene glycols, polypropylene glycols or polytetrahydrofurans, block copolymers of ethylene oxide and propylene oxide or block copolymers of ethylene oxide, propylene oxide and butylene oxide in which the alkylene oxide units are present in random distribution or in the form of blocks. Preference is given to using, from the group of the diols and polyetherols, ethylene glycol, neopentylglycol, diethylene glycol, triethylene glycol, tetraethylene glycol, pentaethylene glycol and hexaethylene glycol.

Suitable amino alcohols include for example 2-aminoethanol, 2-(N-methylamino)ethanol, 3-aminopropanol and 4-aminobutanol.

Suitable diamines include for example ethylenediamine, propylenediamine, 1,4-diaminobutane and 1,6-hexamethylenediamine and also α,ω-diamines preparable by amination of polyalkylene oxides, especially polyethylene oxides with ammonia.

Suitable polyesterols include those which are customarily used for preparing polyurethanes, for example reaction products of phthalic acid and diethylene glycol, isophthalic acid and 1,4-butanediol, isophthalic acid/adipic acid and 1,6-hexanediol and also of adipic acid and ethylene glycol.

To prepare the preproducts formed from the diisocyanates and the compounds having active hydrogen atoms, it is also possible to use mixtures of these compounds, for example mixtures of a diol and a polyesterol or of a diol and polyetherols. Up to 3 mol % of said compounds in the mixtures may be replaced by triols or triamines. Suitable triols may include for example glycerol, trimethylolethane and trimethylolpropane. Suitable triamines include in particular diethylenetriamine and dipropylenetriamine.

In a preferred embodiment, the preproducts are prepared using as compounds having active hydrogen atoms at least 5 mol % of a polylactate diol of the general formula I

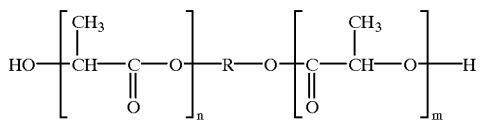

(I)

of a poly-ε-caprolactonediol of the general formula II

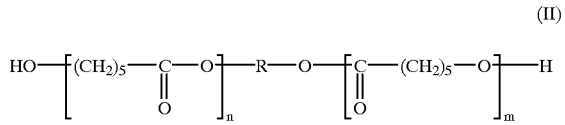

(II)

or of a polyamide diamine of the general formula III

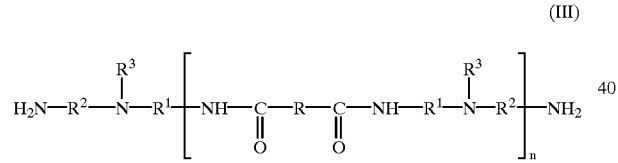

(III)

in each of which

R is $C_2$- to $C_8$-alkylene, $C_5$- to $C_8$-cycloalkylene or phenylene, $R^1$ and $R^2$ are each $C_2$- to $C_8$-alkylene, $R^3$ is $C_1$- to $C_4$-alkyl, phenyl or $C_7$- to $C_{10}$-phenylalkyl, and n and m are each from 1 to 30.

Suitable $C_2$- to $C_8$-alkylene for R, $R^1$ and $R^2$ includes in particular 1,2-ethylene, 1,3-propylene, 1,4-butylene and 2,2-dimethyl-1,3-propylene, but also 1,2-propylene, 1,2-butylene, 2,3-butylene, pentamethylene, hexamethylene, heptamethylene and octamethylene.

Suitable $C_5$- to $C_8$-cycloalkylene R includes in particular the group of the formula

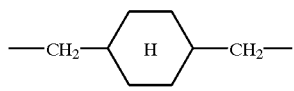

but also 1,3-cyclopentylene, 1,3-cyclohexylene, 1,4-cyclohexylene, 1,4-cycloheptylene or groups of the formulae

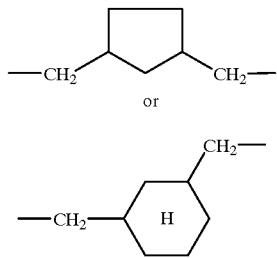

Suitable phenylene R is o-, m- and especially p-phenylene.

Suitable $C_1$- to $C_4$-alkyl for $R^3$ and also for the ($C_1$- to $C_4$-alkyl) phenylene diisocyanates includes in particular methyl and ethyl, but also n-propyl, isopropyl, n-butyl, isobutyl, sec-butyl and tert-butyl.

Suitable $C_7$- to $C_{10}$-phenylalkyl includes in particular benzyl and 2-phenylethyl, but also o-, m- and p-methylbenzyl, 3-phenylpropyl and 4-phenylbutyl.

n and m are each preferably from 1 to 15, especially from 1 to 7.

A highly suitable example of a polyamidediamine III is the condensation product of k mol of adipic acid and (k+1) mol of N-methyldipropylenetriamine, k being from 2 to 5.

The compounds of group (b) preferably include diols, amino alcohols, diamines or triamines with quaternary or protonated amine nitrogen atoms, since charged nitrogen atoms strongly increase the solubility of the polyureas to be used according to the present invention.

In a preferred embodiment, the compounds of group (b) comprise one or more compounds of the general formulae IV to XI

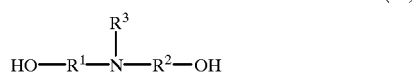

(IV)

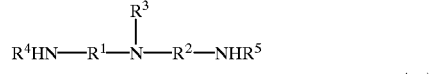

(V)

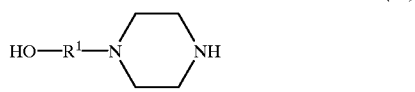

(VI)

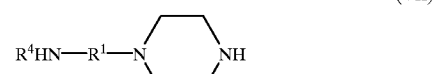

(VII)

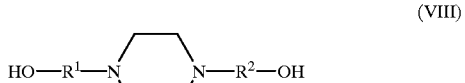

(VIII)

(IX)

-continued

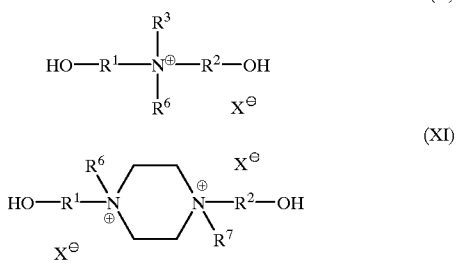

where
- $R^1$ and $R^2$ are each $C_2$- to $C_8$-alkylene,
- $R^3$, $R^6$ and $R^7$ are each $C_1$- to $C_4$-alkyl, phenyl or $C_7$- to $C_{10}$-phenylalkyl,
- $R^4$ and $R^5$ are each hydrogen or $C_1$- to $C_4$-alkyl, and
- $X^\ominus$ is chloride, bromide, iodide, $C_1$- to $C_4$-alkyl sulfate or half the stoichiometric amount of sulfate.

Advantageously the polyurethanes or polyureas are quaternized or protonated prior to the use according to the present invention, unless a quaternized or protonated compound (b), eg. X or XI, was used from the start.

The individual definitions of $C_2$- to $C_8$-alkylene, $C_1$- to $C_4$-alkyl and $C_7$- to $C_{10}$-phenylalkyl are subject to the above remarks.

As is customary in the making of polyurethanes and polyureas, chain extenders can be used. Suitable chain extenders include for example hexamethylenediamine, piperazine, 1,2-diaminocyclohexane, 1,3-diaminocyclohexane, 1,4-diaminocyclohexane, neopentanediamine and 4,4'-diaminodicyclohexylmethane.

The above-described polyurethanes and polyureas are preferably obtainable by reacting the diisocyanates with the reaction partners for the diisocyanates under an inert gas atmosphere in an inert solvent, eg. methyl ethyl ketone in the case of a compound having OH groups and water or an alcohol such as ethanol in the case of compounds having NH groups, at temperatures from 50 to 130° C. in the case of compounds having OH groups and from 5 to 30° C. in the case of compounds having NH groups. This reaction may if desired be carried out in the presence of chain extenders in order that polyurethanes or polyureas having higher molecular weights may be obtained. The reaction can be speeded up with catalysts such as organotin compounds, eg. dibutyltin dilaurate, especially in the case of reactants having OH groups. As is customary in the making of polyurethanes, the reaction partners for the diisocyanates and the diisocyanates themselves are advantageously used in a molar ratio of from 0.8:1 to 1.1:1.

The amine number of the polyurethanes or polyureas are determined by the composition, especially by the proportion in the mixture of the compounds having tertiary, quaternary or protonated tertiary amine nitrogen atoms. The amine number is preferably within the range from 65 to 180, especially from 70 to 170, particularly preferably from 75 to 160, very particularly preferably from 80 to 150.

In the synthesis of the polyurethanes and polyureas described, the proportion of compounds having NH groups, based on the amount of compounds having OH groups, is generally from 35 to 100% by weight, preferably from 40 to 100% by weight, in particular from 50 to 100% by weight.

The polyurethanes and polyureas usually have K values of from 15 to 100, preferably from 20 to 50, determined by the method of H. Fikentscher in 0.1% strength by weight solutions in N-methylpyrrolidone at 25° C. and pH 7.

The glass transition temperatures of the polyurethanes and polyureas described are usually within the range from 25 to 140° C.; below 25° C. the polyureas no longer have adequate film-forming properties. A preferred range is from 50 to 120° C. The glass transition temperature can be determined by the method of ASTM D 3418.

The polyurethanes and polyureas described, having cationic groups, are generally, especially if charges are present, readily alcohol- and water-soluble or at least dispersible in alcohol and water without emulsifiers. Alcohol is hereto understood as meaning especially short-chain alkanols such as methanol, ethanol, isopropanol or n-propanol. Charged cationic groups can be created in the polyureas from the tertiary amine nitrogen atoms present either by protonation, for example with carboxylic acids such as lactic acid, or by quaternization, for example with alkylating agents such as $C_1$- to $C_4$-alkyl halides or sulfates. Examples of such alkylating agents include ethyl chloride, ethyl bromide, methyl chloride, methyl bromide, dimethyl sulfate and diethyl sulfate.

Since some of the polyurethanes and polyureas described are novel substances, the present invention also relates to these novel substances.

The present invention accordingly provides polyurethanes and polyureas formed from (a) $C_2$- to $C_8$-alkylene diisocyanates, $C_5$- to $C_{10}$-cycloalkylene diisocyanates, phenylene diisocyanates or ($C_1$- to $C_4$-alkyl)-phenylene diisocyanates, which each may have already been reacted with one or more compounds selected from the group consisting of diols, amino alcohols, diamines, polyesterols, polyamidediamines and polyetherols each with a number average molecular weight of up to 2000, although up to 3 mol % of the last-mentioned compounds may be replaced by triols or triamines and the diols and aminoalcohols may contain one or more tertiary, quaternary or protonated tertiary amine nitrogen atoms and at least 5 mol % of the compounds previously reacted with the diisocyanates comprise a polylactate diol of the general formula I

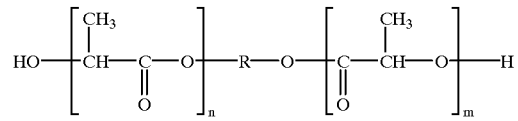

a poly-ε-caprolactonediol of the general formula II

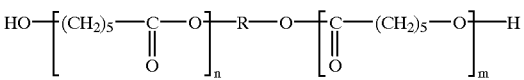

or a polyamide diamine of the general formula III

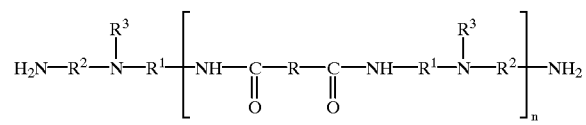

in each of which
R is $C_2$- to $C_8$-alkylene, $C_5$- to $C_8$-cycloalkylene or phenylene, $R^1$ and $R^2$ are each $C_2$- to $C_8$-alkylene, $R^3$ is $C_1$- to $C_4$-alkyl, phenyl or $C_7$- to $C_{10}$-phenyl-alkyl, and n and m are each from 1 to 30,
and (b) at least one diol, primary or secondary amino alcohol, primary or secondary diamine or primary or secondary triamine each with one or more tertiary, quaternary or protonated tertiary amine nitrogen atoms
and having a glass transition temperature of at least 25° C. and an amine number of from 50 to 200, based on the non-quaternized or-protonated compounds, or other salts of these polyurethanes and polyureas.

The present invention provides in particular those polyurethanes and polyureas of the above-defined composition wherein the compounds of group (b) comprise one or more compounds of the general formulae IV to XI

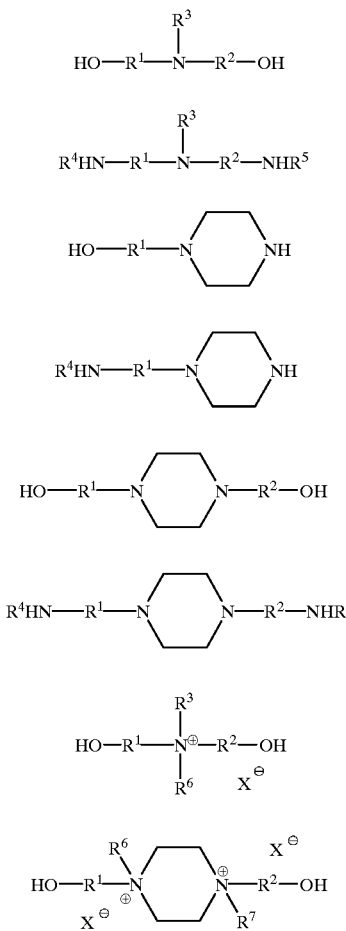

where
$R^1$ and $R^2$ are each $C_2$- to $C_8$-alkylene, $R^3$, $R^6$ and $R^7$ are each $C_1$- to $C_4$- alkyl, phenyl or $C_7$- to $C_{10}$-phenylalkyl, $R^4$ and $R^5$ is chloride, bromide, iodide, $C_1$- to $C_4$-alkyl sulfate or half the stoichiometric amount of sulfate.

The polyureas described are generally at least partially biodegradable.

The polyurethanes and polyureas described are used not only in hair cosmetics as film formers in sprays, mousses, fixatives or gels or as conditioners in hair rinses or shampoos but also for creams and in the pharmaceutical sector as tablet coatings and binders.

The present invention thus also provides cosmetic and pharmaceutical preparations comprising effective amounts of the cationic polyurethanes or polyureas described or other salts thereof. An effective amount generally ranges, depending on the use, from 0.1 to 50% by weight, in particular from 0.5 to 30% by weight, based on the preparation.

If the polyurethanes and polyureas described are used as hair dressings with film-forming properties, they are usually employed in the form of aqueous or ethanolic solutions (lotions). The solids content of these lotions ranges from 0.1 to 30, preferably from 1 to 15, % by weight of polyurethane or polyurea or of a salt thereof.

EXAMPLE

General Method of Preparation

In a four-neck flask equipped with stirrer, dropping funnel, thermometer, reflux condenser and apparatus for working under nitrogen, the OH-containing compounds indicated in the table are dissolved in methyl ethyl ketone by heating the reaction mixture with stirring to a temperature of about 80° C. As soon as everything has dissolved, the reaction mixture is cooled down to about 60° C. and the particular diisocyanate indicated in the table is added dropwise with stirring. The reaction temperature rises. At an internal temperature of 90° C. the reaction mixture is then stirred until the isocyanate group content of the mixture remains virtually constant. Thereafter the reaction mixture is cooled down to a temperature within the range from 10° C. to 20° C., ethanol is added, and the NH-containing compounds indicated in the table and optionally chain extenders with NH groups are gradually added dropwise at that temperature. Stirring of the reaction mixture is then continued within this temperature range until the isocyanate group content has dropped to a constant value. If no chain extender was added, the remaining isocyanate groups are deactivated by adding amines, for example 2-amino-2-methyl-1-propanol. A protonating or quaternizing agent as per the table is added to produce the end product. The bulk of the methyl ethyl ketone and of the ethanol is distilled off under reduced pressure at about 40° C. The remaining ethanol is removed at 50° C. in a vacuum drying cabinet. Drying leaves an elastic to very hard product which is soluble/dispersible in ethanol and water.

If only NH-containing compounds are reacted with the diisocyanate, the reaction is straight away carried out at from 10° C. to 20° C. in ethanol, without methyl ethyl ketone.

Instead of ethanol it is also possible to use water. The methyl ethyl ketone or ethanol solvent can then be distilled off at 40° C. and reduced pressure after the reaction has ended, so that an aqueous solution or dispersion of the polyurea with the properties indicated in the table is obtained directly.

The abbreviations in the table have the following meanings:

| | |
|---|---|
| MDEA: | N-methyldiethanolamine |
| MDPTA: | N-methyldipropylenetriamine |
| AEP: | 2-aminoethylpiperazine |
| P(MIS-EG): | poly(lactic acid-ethylene glycol) ($M_w$ = 500 g/mol) |
| P(IPS/ADS-VI): | polyesterol from isophthalic acid adipic acid and 1,6-hexanediol ($M_w$ = 1000 g/mol) |
| NPG: | neopentylglycol |
| IPDI: | isophorone diisocyanate |
| MIS: | lactic acid |
| DES: | diethyl sulfate |
| NMP: | N-methylpyrrolidone |
| | readily soluble |
| disp: | dispersible |

TABLE

| Example No. | Composition [mol fraction] of components (a), (b) and optionally chain extender | Amine No. | Protonating or quaternizing agent | K value (0.1% strength by weight) in NMP | Glass transition temperature $T_G$ [° C.] | Solubility (5% by weight) Ethanol | Solubility (5% by weight) Water |
|---|---|---|---|---|---|---|---|
| 1 | MDEA [1], MDPTA [0.5], IPDI [1.5] | 160 | MIS [1.5] | 40.4 | 69 | 1 | 1 |
| 2 | MDPTA [0.8], piperazine [0.2], IPDI [1] | 126.3 | MIS [0.8] | 47.5 | 76 | 1 | 1 |
| 3 | MDPTA [1], AEP [1], IPDI [2] | 156.3 | MIS [2] | 45.2 | 82 | 1 | 1 |
| 4 | P(MIS-EG) [0.2], MDPTA [0.6], AEP [0.2], IPDI [1] | 103.4 | MIS [0.8] | 20.3 | 49 | 1 | disp |
| 5 | P(IPS/ADS-VI) [0.5], NPG [2], AEP [3], MDPTA [1], IPDI [6.5] | 83.6 | MIS [4] | 34 | 72 | 1 | disp |
| 6 | P(IPS/ADS-VI) [0.1], MDPTA [0.7], AEP [0.2], IPDI [1] | 112 | DES [0.9] | 44.2 | 67 | 1 | 1 |

To demonstrate the use as hair dressing, the following formulations were prepared:

| A) Aerosol hairspray (purely ethanolic) | |
|---|---|
| Product as per Example 5 | 2% by weight |
| Ethanol absolute | 73% by weight |
| Dimethyl ether | 25% by weight |
| B) Aerosol hairspray (aqueous ethanolic) | |
| Product as per Example 5 | 3% by weight |
| Water distilled | 12% by weight |
| Ethanol absolute | 60% by weight |
| Dimethyl ether | 25% by weight |
| C) Hair fixative lotion (aqueous-ethanolic) | |
| Product as per Example 5 | 4% by weight |
| Water distilled | 64% by weight |
| Ethanol absolute | 32% by weight |

Hair treated with A by the usual method had a curl retention value of 92% and a bending stiffness of 129 p. Hair treated in similar fashion with a commercial hair setting composition had curl retention values of 35% (with N-vinylpyrrolidone-vinyl acetate copolymer) and 90% (with N-vinylpyrrolidone-tert-butyl acrylate-acrylic acid copolymer) and bending stiffness values of 59 p and 69 p, respectively.

The bending stiffness test used as a measure of the setting effect was carried out as described in Parfums, cosmetiques, arômes No. 89, October–November 1989, 71. It was also presented at the BASF "Cosmeticon" Symposium on May 10–11, 1990 in Heidelberg. The test indicates which force is necessary to bend a strand of hair which has been treated with a film-forming polymer solution until the polymer film breaks. The greater the force, the higher the setting effect.

We claim:

1. A method of fixing, controlling or shaping hair, comprising applying to hair in need thereof a composition comprising a cationic polyurethane or polyurea in an amount from 0.1 to 50% by weight effective to impart curl retention and bending stiffness to the hair, said cationic polyurethane or polyurea being formed from
   (a) at least one diisocyanate or reaction product thereof with one or more compounds containing two or more active hydrogen atoms per molecule, and
   (b) at least one diol, primary or secondary amino alcohol, primary or secondary diamine or primary or secondary triamine each with one or more tertiary, quaternary or protonated tertiary amine nitrogen atoms and having a glass transition temperature of at least 25° C. and an amine number of from 50 to 200, based on the non-quaternized or non-protonated compounds, or other salts of these polyurethanes and polyureas.

2. The method as claimed in claim 1 wherein the compounds of group (a) comprise $C_2$- to $C_8$-alkylene diisocyanates, $C_5$- to $C_{10}$-cycloalkylene diisocyanates, phenylene diisocyanates or ($C_1$- to $C_4$-alkyl)phenylene diisocyanates, which each may have already been reacted with one or more compounds selected from the group consisting of diols, amino alcohols, diamines, polyesterols, polyamidediamines and polyetherols each with a number average molecular weight of up to 2000, although up to 3 mol % of the last-mentioned compounds may be replaced by triols or triamines and the diols and aminoalcohols may contain one or more tertiary, quaternary or protonated tertiary amine nitrogen atoms.

3. The method as claimed in claim 1 or 2 wherein the diisocyanate reaction products comprise at least 5 mol % of a polylactate diol of the general formula I

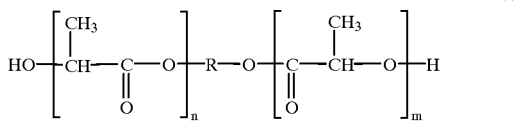

of a poly-ε-caprolactonediol of the general formula II

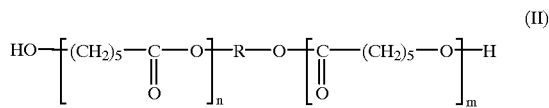

or of a polyamide diamine of the general formula III (III)
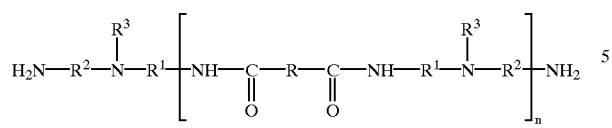

where

R is $C_2$- to $C_8$-alkylene, $C_5$- to $C_8$-cycloalkylene or phenylene, $R^1$ and $R^2$ are each $C_2$- to $C_8$-alkylene, $R^3$ is $C_1$- to $C_4$-alkyl, phenyl or $C_7$- to $C_{10}$-phenylalkyl, and n and m are each from 1 to 30.

4. The method as claimed in claim 1 wherein the compounds of group (b) comprise one or more compounds of the general formulae IV to XI (IV)
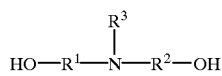

(V)
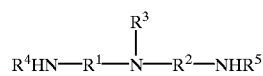

(VI)
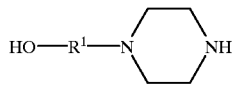

(VII)
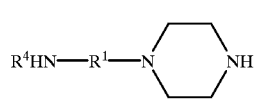

(VIII)
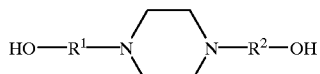

(IX)
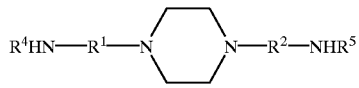

(X)
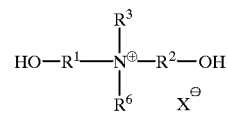

(XI)
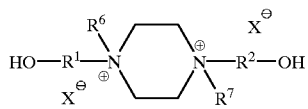

where $R^1$ and $R^2$ are each $C_2$- to $C_8$-alkylene, $R^3$, $R^6$ and $R^7$ are each $C_1$- to $C_4$-alkyl, phenyl or $C_7$- to $C_{10}$-phenylalkyl, $R^4$ and $R^5$ are each hydrogen or $C_1$- to $C_4$-alkyl, and $X^\ominus$ is chloride, bromide, iodide, $C_1$- to $C_4$-alkyl sulfate or half the stoichiometric amount of sulfate.

* * * * *